United States Patent [19]

Vaillancourt

[11] Patent Number: 4,936,832

[45] Date of Patent: Jun. 26, 1990

[54] AMBULATORY DISPOSABLE INFUSION DELIVERY SYSTEM

[76] Inventor: Vincent L. Vaillancourt, 14 Bunyan Dr., Livingston, N.J. 07039

[21] Appl. No.: 377,640

[22] Filed: Jul. 10, 1989

Related U.S. Application Data

[62] Division of Ser. No. 934,510, Nov. 24, 1986, Pat. No. 4,867,743.

[51] Int. Cl.$^5$ ............................................. A61M 37/00
[52] U.S. Cl. .................................... 604/131; 604/151; 128/DIG. 12
[58] Field of Search ............................ 604/131–135, 604/151, 152, 207, 214, 218, 236, 240, 245, 246; 128/DIG. 12

[56] References Cited

U.S. PATENT DOCUMENTS 4,381,006 4/1983 Genese ................................. 604/135
4,636,197 1/1987 Chu ...................................... 604/131

Primary Examiner—John D. Yasko
Attorney, Agent, or Firm—Kenyon & Kenyon

[57] ABSTRACT

A compact disposable delivery system is provided which includes a disposable fluid infusion device for infusing fluid under pressure, a restrictor for controlling the fluid flow, a disposable pressure transducer to receive the pressurized fluid, a catheter connected to the transducer to deliver blood pressure pulses thereto and a recording device electronically connected with the transducer to receive the blood pressure pulses. The fluid infusion device includes a piston which is slidably in the housing under the biasing force of a stretched elastomeric tubing.

10 Claims, 3 Drawing Sheets

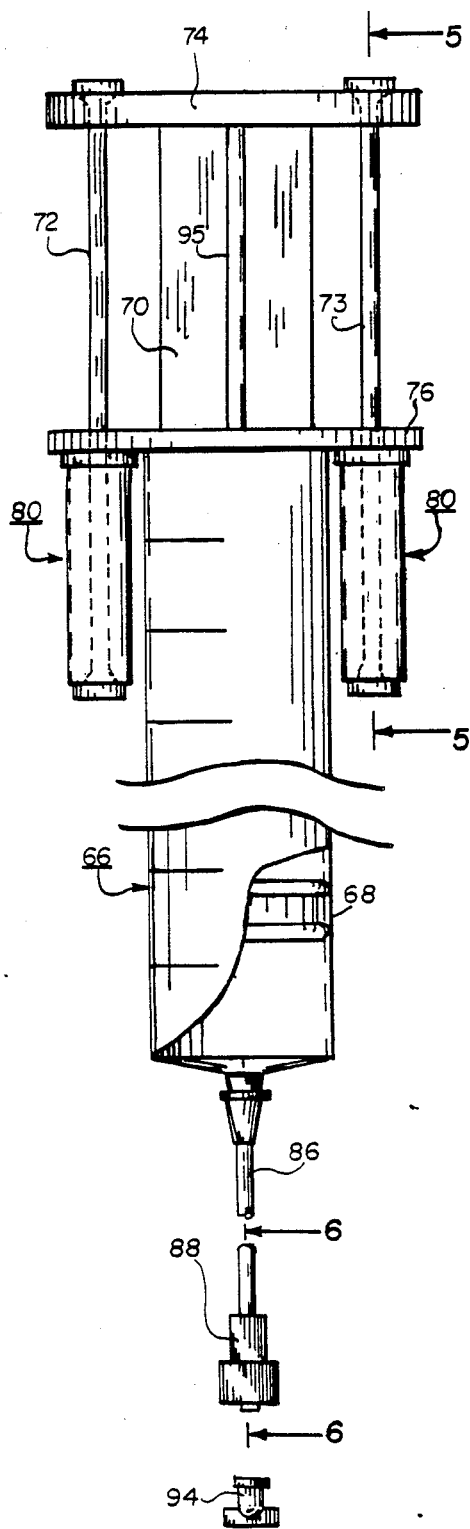
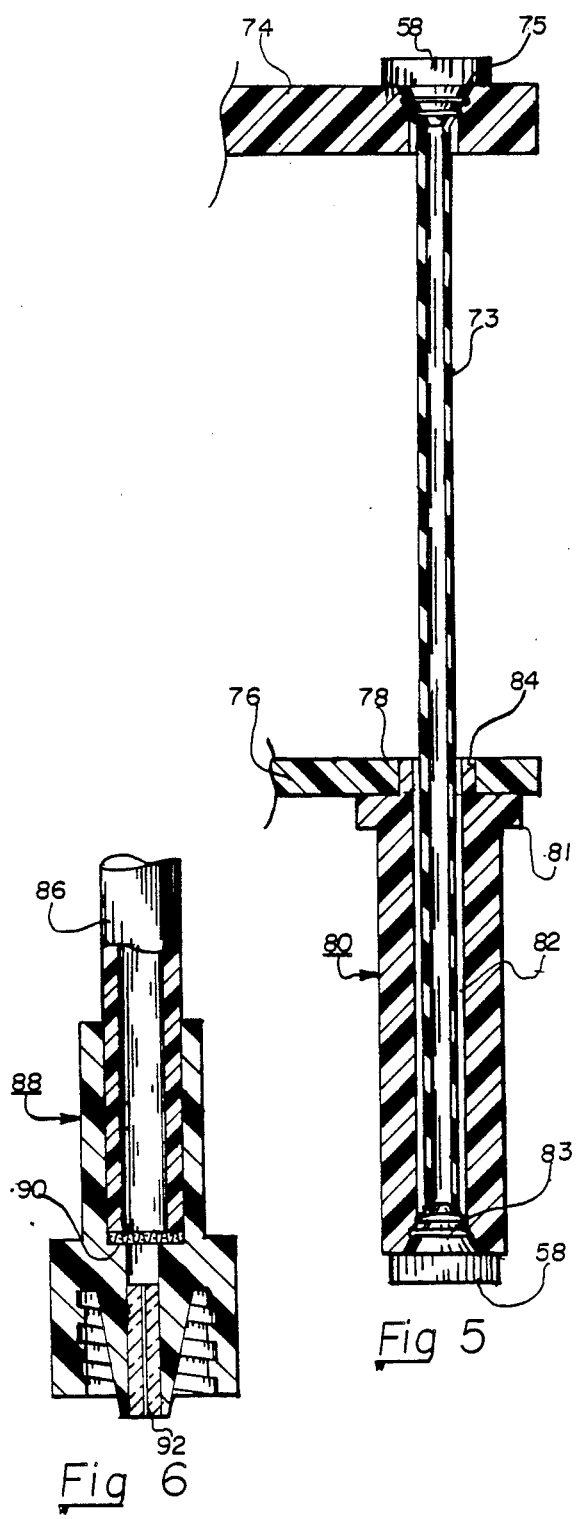
Fig 4
Fig 6
Fig 5

PRIOR ART
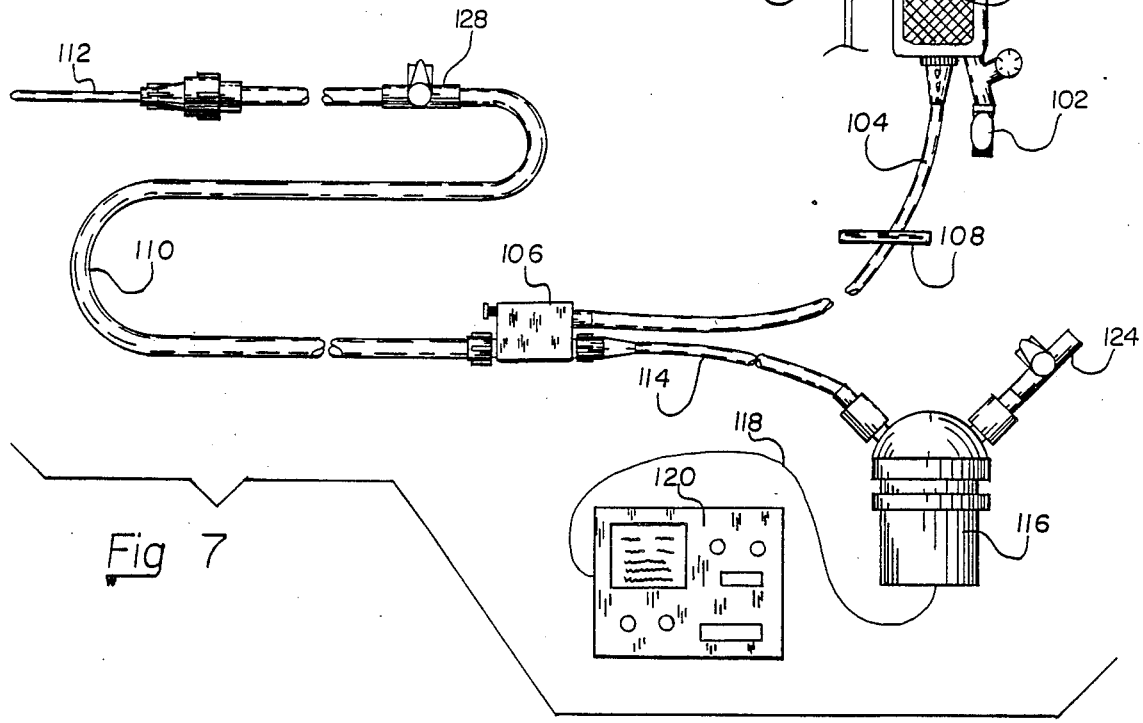
Fig 7
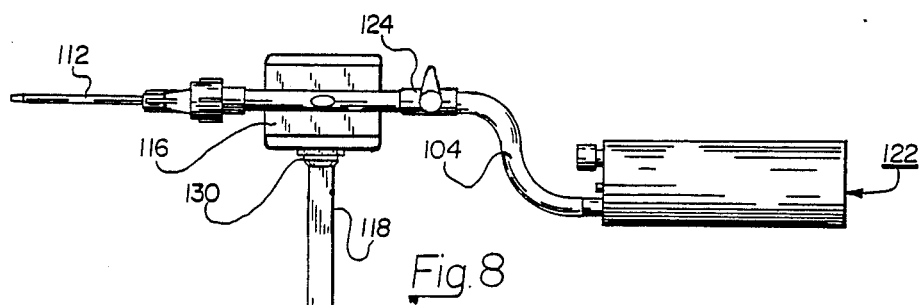
Fig. 8
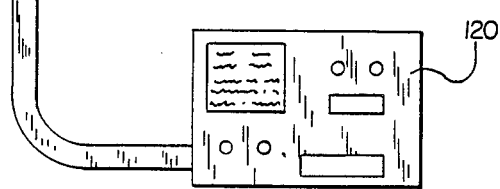

AMBULATORY DISPOSABLE INFUSION DELIVERY SYSTEM

CROSS-REFERENCE TO RELATED APPLICATION

This is a division of application Ser. No. 07/934,510, filed November 24, 1986, now U.S. Pat. No. 4,867,743.

This invention relates to an ambulatory disposable delivery system utilizing a bias-actuated piston in a small housing.

BACKGROUND OF THE INVENTION

1. FIELD OF THE INVENTION

This invention relates to an improvement in a disposable delivery system that provides a continuous flow of fluid to a patient. This invention also relates to a simplified method for physiological blood pressure monitoring and eliminating the need for Heparin in "Heparin Lock" devices.

2. DESCRIPTION OF THE PRIOR ART

Many infusion systems have been proposed and sold for the dispensing of drugs into a patient. With few exceptions, these systems contain both reusable (hardware components) and disposable parts. These systems include, for the most part, electrical components, with their attendant costs and limitations. The system as shown and described in the present application has an infusion delivery system that does not use or utilize electrical or electronically-related components, and this delivery system is completely disposable after a one-time use.

The delivery of medication may include a catheter as the vascular access device or dispensing may be through a needle penetrating an implanted vascular access port which in turn is connected to a blood vessel using an internal catheter. The delivery system of this medication includes a fluid reservoir. Fluid delivery is continuous for an extended and determined period of time. Devices of this type are preferably light in weight and pocket accessible. A termination of use occurs when the medical procedure is completed. The device is then simply discarded. At present, most, if not all, disposable ambulatory medicator infusion devices employ an elastomeric bladder which is caused to be expanded as the drug is fed or otherwise flows into the bladder. The delivery is dependent upon the capability of the bladder to expand and contract. For example, U.S. Pat. No. 3,486,539 describes a structure employing a bladder as a means of storage as well as contraction to provide for expulsion of fluid while providing pressure. Such a dispensing device anticipates filling a bladder through a front-connected needle with a flow metering restrictor. U.S. Pat No. 3,993,069 describes a system having an expansible elastomeric bladder and a separate flow-control device and outer flow restrictor. U.S. Pat. No. 4,318,400 describes an elastomeric bladder-powered infuser and a tubular cas enclosure to prevent excessive expansion of the bladder. Drugs are fed through a needle and syringe to the bladder through a resilient plug at the rear of the device. U.S. Pat. No. 4,386,929 describes a structure similar to that of U.S. Pat. No. 4,318,400.

U.S. Pat. No. 4,419,096 describes an apparatus of similar construction as above with an added lumen and bulbar filler portions to establish the contracted shape of the elastomeric bladder when the contents are, or substantially are, expelled.

In the disclosure to be hereinafter more fully described, the delivery of fluid to a catheter may include a flow-stopping device. The fluid flow may be used with a pressure transducer to produce waveforms of blood pressure, with electrical signals from the pressure transducer sent to a display and monitor. In another arrangement, medication (drugs) may be injected using a Y-block arrangement downstream of the pressure piston. The piston as carried in a housing may be advanced by external means.

SUMMARY OF THE INVENTION

It is an object of this invention to provide, and it does provide, an infusion device that may be filled with a fluid, using conventional means such as a hypodermic syringe, with the needle inserted through a resilient plug. This device utilizes a movable piston, in one embodiment, attached to a rubber tube and the like. In another embodiment, the piston is moved by external means.

Another object of this invention is to provide, and it does provide, a small, lightweight cylindrical apparatus which is filled with fluid through a delivery device such as a hypodermic needle attached to a syringe and/or a pressurized container. The inflow of fluid causes a slideable piston to move rearwardly in a tubular barrel and elongate an elastomeric member. In this manner, energy is stored which is subsequently used to deliver this same fluid to an attached connector device to a patient's previously inserted catheter. This fluid is delivered at a predetermined rate of flow governed by the force provided by the stretched resilient member. This rate is thus predictable with a determined restrictor size or delivery tubing geometry.

It is a further object of this invention to provide, and it does provide, a small, lightweight fluid-delivery system providing a continual, small flow to a catheter, with a pressure transducer interposed in the delivery system to measure blood pressure waveforms, and with this pressure transducer producing electrical signals sent to a display and monitoring recorder.

It is still a further object of this invention to provide, and it does provide, a fluid-delivery system having a fluid container with the delivery end flow-connected to tubing leading to a Y-block connection, providing an access port into which a needle of a syringe may be inserted to administer a drug. This Y-block is flow-connected to an indwelling catheter.

It is a further object of this invention to provide, and it does provide, a pressurized fluid-delivery system utilizing exterior resilient means to provide a driving force to move the piston forwardly in the fluid-delivery system.

This device is shown so as to illustrate changes of construction and use. Essentially, a sliding piston is carried in a tubular confine of selected length. In one embodiment, the rear of this tubular chamber may be closed by a cap to prevent contamination during filling and, when used, having a small aperture or air vent filter to prevent the development of negative pressure. The forward end of this chamber is connected to a tubing set which includes means for injecting drugs/fluids into a delivery system leading to the patient. An ingress means, such as a resilient plug, is provided for the insertion of the fluid (drug) into the tubing chamber, and with the fluid inflow the slideable piston is moved toward the rear of the chamber. This piston is connected at its forward end to an elastomeric strand member, preferably a rubber tube, which provides the compression force (rubber tube in tension) to draw the piston toward and to the front end of the chamber.

In two of the embodiments, the fluid container is shown with a movable sliding piston, which is more fully described below. In one embodiment, the piston is moved by an elastomeric member within the housing, and in the other the piston is moved by stretched elastomeric members exterior of the housing. In both embodiments, the piston moves toward the end wall so as to produce a minimal to zero final fluid volume. In both constructions, the elastomeric member utilizes the stretch force to expel the stored fluid from the housing. The leading edge of the piston may be used as a measuring means (similar to present use in disposable syringes) to measure accurately the quantity of medication infused or remaining.

The fluid-delivery system may utilize a Y-block type of connection which is interposed downstream of the fluid-flow control means. The Y-block is flow-connected to an indwelling catheter. This Y-block has one port closed with a resilient cover adapted to be pierced by a needle of a syringe to deliver drugs to the inflow stream. This same fluid-delivery system without the Y-block and with a stopcock may be connected to a pressure transducer so that, when a catheter is inserted into the artery of a patient, the fluid conducts pressure pulses to said pressure transducer and from this pressure transducer sends electrical signals to a conventional monitor recorder and display.

The fluid-delivery system of this invention utilizes a small container, usually cylindrical, having a discharge end provided with a tubing connecting means to which or on which a flexible non-elastic tubing conductor is removably attached. Discharge tubing from the device usually includes a luer lock hub connector which may include a filter and flow-control restrictor. All units are small, light in weight, and are designed for a patient to use inconspicuously (usually under clothing). All embodiments are silent in their use and, except for their connection to the vascular access device in the patient, are entirely self-contained. The fluid flow is controlled, with no adjustments required, and permits this device to be used with both hospital in-patients and out-patients (Home Therapy Programs). The administration of fluid through this infusion device is continuous to the patient. The flow of fluid is dependent upon the force developed by the stretched elastomeric member which is in tension in combination with the fluid-flow properties (primarily viscosity), piston friction resistance, and frictional resistance through the fluid conduit.

In one embodiment, the fluid to be delivered is flowed into the cylinder through a one-way valve and/or injection port. The inflow of fluid under pressure into the cylinder causes the piston to move rearwardly as this fluid fills the cylinder. The rubber tubes that supply the compressing force are stretched (placed under tension) until the cylinder is filled with the desired amount. The injection port is then closed.

In the embodiments illustrated in the FIGS., there are shown two housings in which a piston is moved in a tubular barrel. In one, an elastomeric member is disposed within this tubular barrel, and in the other the piston is moved by stretched elastomeric member(s) disposed outwardly of the housing. These embodiments illustrate a means of construction. Although a fluid-delivery means is shown, there are provided use arrangements, and any disposable fluid-delivery system may be used for the systems to be hereinafter more fully shown and described.

Generally, piston friction and fluid-flow resistance properties are determined through design. By placing a restrictor in the fluid line (variable or fixed), the flow rate can be predicted for a given fluid. Alternately (not shown), the restrictor may be external. The external control may be a fixed or variable valve such as a stopcock. There may be added friction force (drag) to the piston which is used to control the rate of fluid flow.

It is anticipated that the device or system will hold about two to sixty cc.s of fluid, and as a fluid be dispensed through the connected tubing to a catheter/vascular access means in the patient. As this device is very lightweight and small, the patient is not restricted but may be ambulatory. As this tubular cylinder is conventionally made from molded, substantially transparent materials, drugs can be seen visually. The quantity delivered or the quantity remaining is easily and positively verified and, most importantly, it can be ascertained whether or not the drug is contaminated. When the tension member is externally mounted, potential drug-elastomer compatibility concerns are removed.

These systems obviate the need for patient training and/or manipulation such as is required for syringe pumps. These systems are essentially assembled, require minimal professional training with no need for technical skills, and are self-regulating. These systems are tamper-proof in that once a satisfactory hook-up is made, there is no means by which the patient may violate the system without the violation becoming known.

In the several FIGS., the ambulatory disposable infusion delivery system shows in detail the use of a piston in a housing and with propelling force being provided with both internal and external stretched elastomeric members. In one embodiment, a simplified drug-delivery method is shown, and in another embodiment an invasive blood pressure monitoring system is provided. In the drug-delivery system, the need for purging of heparin is removed and, in the other embodiment for blood pressure monitoring, waveform fidelity is substantially increased.

These and other objects and advantages of the invention will become more apparent from the following detailed description taken in conjunction with the accompanying drawings wherein:

BRIEF DESCRIPTION OF THE DRAWINGS

FIG. 4 represents a side view, partly diagrammatic and partly in section, and showing a syringe with added members adapted for mounting exterior and employing elastomeric means for advancing the piston carried therein;

FIG. 5 represents an enlarged, fragmentary sectional view taken on the line 5—5 of FIG. 4 and looking in the direction of the arrows, this enlarged view showing a means for exteriorally securing the elastomeric means;

FIG. 6 represents a fragmentary, sectional side view greatly enlarged so as to show a flow restrictor and connection means, this view taken on the line 6—6 of FIG. 4 and looking in the direction of the arrows;

FIG. 7 represents a diagrammatic "PRIOR ART" showing of an invasive blood pressure monitoring system, and FIG. 8 represents an invasive blood pressure monitoring system which is closely coupled and is adapted to provide a small, continuous fluid flow to and through a transducer to a placed catheter in a patient.

In the following description and in the claims, various details are identified by specific names for convenience. These names are intended to be generic in their application. Corresponding reference characters refer to like members throughout the several figures of the drawings.

EMBODIMENT OF FIG. 1

Figure 3:
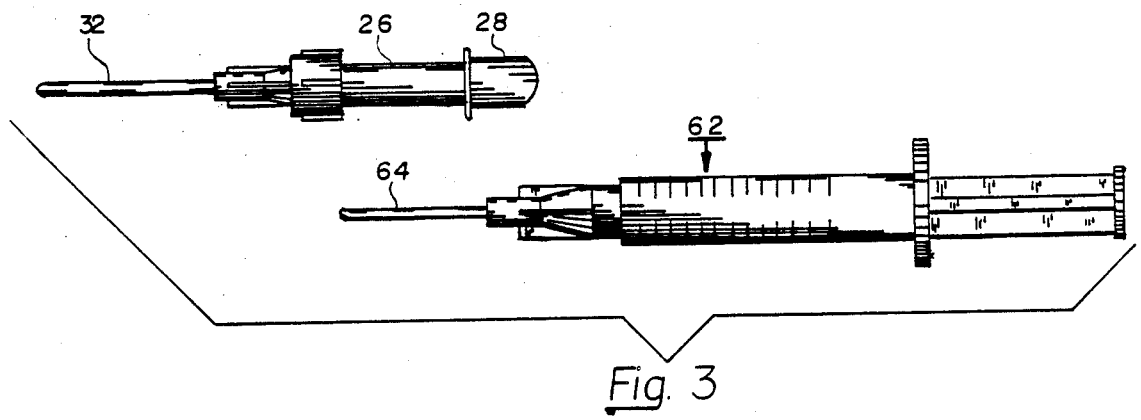
FIG. 3 represents a side view of a "PRIOR ART" apparatus and method for injecting drugs in a catheter placed in a patient.

A preferred use of the fluid infusion device of this invention is for a selected addition of a determined quantity of a fluid (drug or the like) to a fluid delivered from an infusion device. The fluid infusion device, generally identified as 20, is connected to and discharges fluid continuously to a conventional flexible conductor 22. Depicted is a keyhole-type clamp and shut-off 24. This clamp may or may not be used during drug infusion, being dependent upon individual preference. The conductor has one end connected to one side of a Y-block connector 26. This connector has as its other leg an injection site 28 upon which is mounted a rubber resilient cap that is self-sealing after piercing with a needle. From this connector 26, another flexible conductor 30 extends to and is connected to a catheter 32 in the usual manner. It is to be noted that the Y-block may be mounted at the catheter connector, thus eliminating the need for flexible conductor 30.

EMBODIMENT OF FIG. 2

Figure 2:
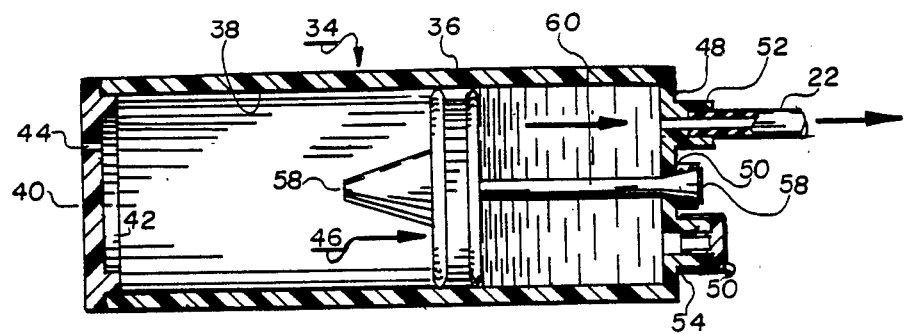
FIG. 2 represents a sectional side view of an infusion delivery apparatus utilizing a secured elastomeric member to move a piston.

As depicted in this FIG. 2 embodiment, a housing, generally identified as 34, is a molding 36 and is formed with a substantially constant bore 38. The rear end of this molding may be closed by a cap 40 having a skirt portion 42 that is a snug fit within said bore 38. In this cap is also provided a vent filter or aperture 44 which allows atmospheric air to enter or that air within the barrel to be expelled so that development of negative or positive pressure within the housing does not occur when and with a sliding motion of a piston 46. This housing is formed with a forward wall 48 in which there are formed three through apertures.

A substantially central aperture is identified as 50 and is provided with an outwardly-extending collar portion having an internal configuration with a taper. Another aperture 52 is also formed with an outwardly-extending collar portion with a stepped bore, and with the larger exterior bore sized to accept and retain the end of tubing 22. The other aperture is identified as 54 and is sized to accept and retain a resilient plug such as 56.

Piston 46 is a structure having an outer member of Teflon (TM duPont), coated rubber or silicone rubber, or a surface treated or coated to minimize stick-slip variations in friction and provide minimum friction resistance. This member is provided with ribs or rings. A through aperture and a taper portion are provided in this piston structure. A small, tapered plug 58 is adapted to receive and retain an elastomeric tubing 60 brought into and through the piston 46.

The use and actuation of this infusion device is detailed in the U.S. Pat. No. 4,813,937.

EMBODIMENT OF FIG. 3

This showing is a known and conventional arrangement used to provide injecting of drugs. This is "prior art" as to the present invention. Conventionally, a catheter 32 (similar to that in FIG. 1) is provided with an injection cap 28 and is placed in a patient to provide and obtain continuous access to a patient's vein without the need for additional venipunctures. These devices are known as "Heparin Locks."

To infuse a bolus of medication, the following procedure, often known as SASH, is followed: A needle syringe is filled with physiological saline solution and is injected through cap 28 to flush out the Heparin present in the system (catheter 32 and injection port 26). This Heparin is initially present to prevent clotting in the catheter 32 and injection port 26. This physiological saline solution is used to remove the Heparin so that a subsequent medication being administered does not interact with the Heparin and crystallize, separate, precipitate, etc., as do many medications which have limited compatibility with Heparin.

After injecting the physiological saline solution into cap 28 of said "Heparin Lock" device, the syringe is discarded and a second syringe containing the prescribed medication is injected through cap 28 and administered to the patient. Any residue medication must now be removed from the "Heparin Lock" device by a second injection of physiological saline solution. Normally, a second prefilled needle syringe is used to flush out the "Heparin Lock" device by injecting through cap 28. After flushing with physiological saline solution, this second syringe is now removed. A third prefilled syringe containing Heparin is used to refill the "Heparin Lock" device with Heparin. The Heparin prevents blood from clotting and in this manner lumen patency is maintained.

Figure 1:
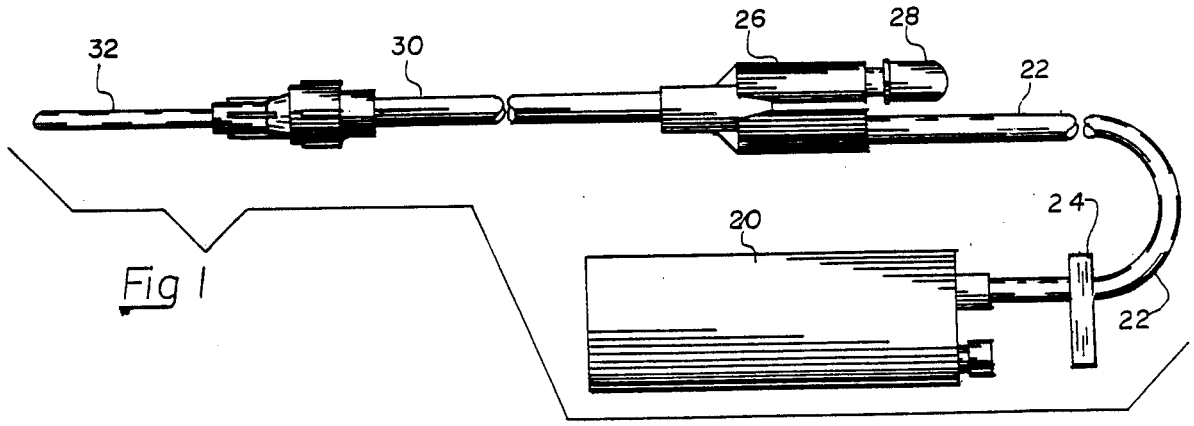
FIG. 1 represents a diagrammatic and partly expanded side view of an infusion device connected to a Y-block and catheter. The Y-block provides a means for the addition of a drug to the patient.

The device of FIG. 1, using the small infusion device 20 to feed a small, continuous flow of physiological saline solution to the placed catheter 32, does not require the above SASH procedure. This continually infused solution prevents occluding of the catheter and, as no Heparin is required, an added drug may be injected through the cap 28 in the desired amount and at the desired time. Many patients are adversely affected by Heparin. Hence, the system of FIG. 1 eliminates potential patient complication. The potential deleterious effect of Heparin in the blood of the patient is thus also eliminated. As only the desired drug is added to the delivery system, no Heparin is present which may cause unwanted precipitation, crystallization or separation due to interaction of drugs. In FIG. 3, the resilient cap 28 as used in the SASH "Heparin Lock" procedure may be slightly remote from the catheter apparatus 32. A conventional syringe 62 has a sharpened needle 64 used therewith. This syringe-and-needle assembly is quite conventional and is used in the usual manner to provide the desired fluid to the catheter 32 and cap 28.

EMBODIMENT OF FIGS. 4, 5 and 6

The infusion housing as shown in FIG. 2 anticipates receiving and expelling fluid at a determined fluid flow. In the views of FIGS. 4, 5 and 6, there is shown an alternate infusion device. In this embodiment is illustrated the providing of an infusion device which utilizes a syringe-type member. As depicted, a syringe 66 has a piston 68 which is conventionally constructed with sealing ring(s) and is attached to a piston rod 70. This rod moves the piston in and out, but in this embodiment is moved inwardly by two resilient and elastomeric force members 72 and 73. In the embodiments of FIGS. 4 and 5, these elastomeric members are of rubber tubing, with the outer ends retained in apertures formed in transverse bar portion 74. The retention of the upper end of the elastomeric tubing is in a tapered bore 75 by and with a plug 58. There are two tapered bores 75 in each transverse bar portion. This transverse bar portion is secured to the piston rod 70. The syringe 66 at its larger open end is made with a finger-type grip in the form of a bar 76. In this lip there are formed two through apertures 78. On the underside of the finger-type grip bar 76 is a tubular member 80. Each tubualr member is depicted as having a flange 81 positioned on the underside of finger-type grip bar 76 with a through bore 82. The lower end of this bore is made with a taper 83. Taper plugs 58, like those seen in FIG. 2, are utilized to retain the tubing 60 in the desired tensioned condition.

It is also contemplated that the through apertures 78 in finger-type griup bar 76 may be of a diameter to accommodate protruding locating tubular portions 84, preferably integrally formed as members 80 are molded. These protruding portions 84 are sized to locate and position member 80 in grip bar 76. Preferably, an interference fit of protrusion 84 in aperture 78 or cement is used to provide securing of members 80 in a retained condition.

Although the embodiment of FIGS. 4 and 5 shows two like tubular members 72 and 73, it is, of course, realized that only one member is required when and as there is provided a guideway and guide-slide member on the opposite side of the device. This guide-slide is not shown as many configurations may be provided, including a rod slidable in a mating tube or a dovetail arrangement utilizing a tongue and groove apparatus. It is, of course, also realized that members 72 and 73 may be made as one member, with the central portion carried across the exterior portion of transverse bar 74. It is also contemplated that, rather than tubular members 72 and 73, rubber-band material may be utilized.

In the discharge conductor from the syringe 66, there is depicted in the enlarged sectional view of FIG. 6 a flexible conductor 86 that is secured to the discharge end of the syringe by a luer slip or like means. This conductor is mounted in a connector 88 and, as shown, has a luer lock connecting means. A filter 90 may or may not be mounted at the discharge end of conductor 86 so as to remove any unwanted particles before delivery to a patient. A flow restrictor 92 is shown as carried in this connector and is adapted to limit the rate of fluid flow. Another connector 94 is depicted and may be any connector downstream of the infusion device.

USE AND OPERATION OF THE DEVICE OF FGIS. 4, 5 AND 6

This device is to preclude the inclusion of an elastomeric tension member in the fluid reservoir as in FIG. 2. In this embodiment of FIGS. 4 through 6, it is contemplated that a syringe-type member 66 may be utilized. This syringe-type member may be of fifty cc. capacity, or more or less. The syringe-type member and piston are conventional and the piston rod 70 is depicted as having a plurality of ribs 95. These ribs mate with means carried by finger-grip portion 76 to provide means preventing unwanted rotation of this rod 70 in the housing of the syringe-type member 66. The transverse bar portion 74 is thus maintained in the desired orientation with finger-grip portion 76.

Tubular members 80 are brought to grip portion 76 and are aligned with aperture 78 and in coincidence with through bore 82. Cement or pilot means may be provided to insure that the precise alignment is made and maintained. This alignment is also in coincidence with the tapered bore 75 in transverse bar portion 74. A selected length of elastomeric tubing 73 is now fed through these aligned apertures and bores. One end of the tubing is secured in a taper by a tapered plug 58. The elastomeric tubing is stretched to provide a predetermined initial tension. The other end of this tensioned tubing is now secured with another tapered plug 58. The other length of elastomeric tubing 72 is mounted and tensioned in a like manner.

The syringe-type member 66 may have the discharge conductor 86 removed from the small end the grasping the transverse bar 74 and pulling outwardly a determined quantity of fluid is drawn into the syringe 66. This outward movement of piston 68 is against the force of and causes further stretching of elastomeric members 72 and 73. The conductor 86 is now reattached as in FIG. 4 so that the fluid in the syringe 66 may be and is discharged through conductor 86, filter 90 (if provided) and through flow restrictor 92.

The restrictor 92 is depicted in FIG. 6, but other flow control means such as valves (fixed or adjustable), tubing size or external restrictors may be used to control the fluid flow. It is also to be noted that the elastomeric members 72 and 73 are depicted and described are tubing, but other elastomeric constructions are contemplated such as strands. It is only required that the piston 68 be urged toward the closed end by the elastomeric force. The piston is moved outwardly by the attendant and by the force toward the finger grip portion 76. The showing in FIG. 4 has two tubing members 72 and 73 that are equally spaced from the axis of the piston 68. This utilizing of two members is so that the force for expelling is balanced. The showing of the piston rod 70 with ribs 95 is known, but the addition of guide means (not shown) and secured to the finger grip 76 may be a sheet of plastic with appropriate guide means provided. It is only necessary that this guide means provide and insure that alignment is made and continued for the apertures in and for the elastomeric members. If these elastomeric members are in the nature of rubber bands, it is still necessary that initial tension be established and present when the piston 68 is at the expelled position and condition. The tubular portions 80 provide the desired extension of distance for stretching needed to bring elastomeric members 72 and 73 into the desired tensioned condition.

EMBODIMENTS OF FIGS. 7 AND 8

Referring to the embodiments and drawing showing FIGS. 7 and 8, it is to be noted that the infusion device of this application may also be utilized for blood pressure pulse monitoring. In FIG. 7, there is depicted the conventional physiological pressure monitoring system that is widely used in hospitals and the like. This embodiment is labeled "PRIOR ART." As seen in FIG. 7, a flexible bag 98 is shown as carried by an I.V. stand or support 99. The fluid in this bag 98 is pressurized through a pressure cluff 100 by squeezing bulb 102 until the desired pressure is achieved. The pressurized fluid is then delivered through conductor 104 to a restrictor-flush device 106. A keyhole clamp or cutoff 108 is also depicted. From this restrictor-fast flush device 106, fluid is fed through a conductor 110 to a connected catheter 112 placed in the arterial stream of a patient. Blood pressure pulses travel through this fluid path to and through a conductor 114 to a transducer 116. This transducer sends electronic signals through wire coductors 118 to a recording device 120.

In FIG. 8 is depicted the infusion device used as a source for a continuous supply of fluid flow. This infusion device is used with a transducer and electronic recorder. As depicted, an infusion supply device 20 as in FIG. 1 or, using a syringe-type member 66 as in FIG. 4, for the purpose of general indentification, is numbered as 122. The discharge of fluid is through a flexible conductor such as 104, indentified above. A stopcock connector 124 is placed in the delivery tubing 104 so as to zero out the pressure transducer, and provide a port for drug injections. The fluid in tubing 104 is supplied from the supply device 122. The fluid in conductor 104 proceeds through transducer 116 and is delivered at a small flow rate to the catheter 112 through conductor 104.

In this embodiment, the requirement of delivering a continual flow of fluid to the inserted catheter is noted. This continual, small flow of fluid prevents occluding of the catheter lumen so pulse signals may be sent through the fluid to the transducer 116. This representation of the transducer is only symbolic as transducers, particularly disposable types, are in many configurations, and no shape or arrangement is intended to be patentably distinct.

It is to be noted that the prior art device of FIG. 7 is the apparatus usually used and available in hospitals. Physiological saline is usually the supply fluid of choice. The improved device of FIG. 8 contemplates the use of a "disposable"-type transducer 116 which is small in size, lightweight and is easily transportable. Usually, the initial filling of the system of FIG. 8 is by using a syringe filled with a saline solution and, through stopcock 124, filling (priming) the system so as to remove unwanted air. Conductor 104 is filled from pump 122.

This embodiment of FIG. 8 for blood pressure monitoring shows the pressure transducer located near the catheter. This is advantageous in that problems associated with tubing, such as waveform distortion, phase shift and low resonant frequencies, are substantially reduced. The tubing 110 in FIG. 7 is generally three to four feet from catheter to the restrictor-flushing device 106, whereas in FIg. 8 the catheter 112 is physically near or adjacent to the transducer 116. Preferably, this distance is only a few inches. The tubing to the right of the pressure transducer to the supply container 122 has a small lumen to minimize fluid hold-up (not shown). The disposable pressure transducer is small in size and may be of the type as commercially provided by Cobe Labs, Gould Electronics or Sorenson Labs. The wire conductors 118 are conventional. A plug-in connection 130 at the pressure transducer 116 or monitor is provided so that the pressure transducer may be disconnected and the patient readily moved from one area to another.

USE AND OPERATION OF EMBODIMENT OF FIG. 8

The prior art and conventional blood pressure monitoring system, as shown in FIG. 7, are dependent on satisfactory performance of several components as an assembly. In the assembly of FIG. 8, the fluid supply is in the infusion devcie of 122 and is delivered at a controlled flow to conductor 104. A stopcock 124 may close or shut off fluid flow from the infusion-supply device 122 or air initially present in conductor 104 may be bled from the conductor through said stopcock 124.

The infusion supply 122 of FIG. 8 may be any disposable fluid-supply device capable of delivering fluid at a small, continuous flow level to the catheter 112. The discharge of fluid through flexible conductor 104 and stopcock 124 leads to a pressure transducer 116, thence to the catheter 112 which is in the patient. The wires 118 may be disconnected, permitting the patient to be readily moved around. When desired, the wire conductor 118 may be reconnected so that electrical signals can be sent to the monitor 120. The monitor is electrically powered and bulky, hence is generally restricted to one location.

In the system of FIG. 8, it is to be noted that the fluid-supply device 122 may be any of those shown or alternate disposable ambulatory pumps which are capable of continued flow. The system of FIG. 8 does not require a supply of fluid in a bag 98 which contributes to the bulkiness and complexity. The improved waveform fidelity of the system and the elimination of much of the previously associated apparatus in and of FIG. 7 only make the system of FIG. 8 more advantageous in use. The system of FIG. 8 does not require retraining of the attendant, and the potential for trapped air or gas that may occur in the blood pressure monitoring system of FIG. 7 is substantially eliminated.

The use of a disposable infusion delivery system and pressure transducer mounted near the catheter (FIG. 8) provides a vastly improved pressure monitoring system. It is also a novel improvement in the art.

While particular embodiments of the delivery system have been shown and described, it is to be understood that the invention is not limited thereto and protection is sought to be broadest extent the prior art allows.

What is claimed is:
1. A disposable infusion delivery system including
   a housing having a substantially constant bore having a front and rear end;
   a piston slidably mounted in said bore, said piston having outwardly-directed sealing means, a connected rod extending beyond a rear end to provide grasping and manipulating means for in-and-out movement of said piston;
   a front closure portion on said front end of said housing providing a fluid conduit and means for mounting and retaining a fluid tubular conduit through which fluid at least may be expelled from the interior of said housing and into the tubular conduit;
   at least one stretchable elastomeric member in said housing providing a tensioned energy for fluid flow, member having one end secured to said portion rod and with the outer end secured to mounting means provided on the outer surface of said housing, said attached elastomeric member in the fluid-expelled condition having an initial stretch, and a restrictor device controlling the flow of fluid from said housing.

2. A disposable infusion delivery system as in claim 1 in which a syringe has a housing, with the piston therein connected to and movable with and by a rod, and a manipulative rearward movement of the piston draws in fluid, and the forward movement of the piston expelling the fluid is produced by an elasticized and stretched force member.

3. A disposable infusion delivery system including
a housing having a bore;
a transverse lip member secured across said housing with at least two tapered bores therein;
a piston slidably mounted in said housing bore and having a piston rod projecting out of said housing;
a transverse bar secured to and across said piston rod outside said housing with at least two bores therein;
a pair of elongated elastomeric tubular force members, each member extending between said lip member and said bar for biasing said piston into a fluid expelled position;
means securing each respective end of a respective force member in a respective bore of a respective one of said lip member and said bar;
a restrictor device for controlling a flow of fluid from said fluid conduit.

4. A disposable infusion delivery device as set forth in claim 3 wherein said means includes a tubular member disposed in each respective bore to secure a respective end of a tubular force member therein.

5. A disposable infusion delivery system as in claim 4 in which each of the tubular members at its lower end is provided with a tapered socket and the stretched force members are elastomeric tubing portions, with one end secured by a tapered plug in the tapered bore in the transverse bar and with the other end of said tubing passing through the through aperture in the lip and through a bore in a tubular member, and in the stretched condition being secured by a tapered plug to the lower tapered recess in said tubular memeber.

6. A disposable infusion delivery system as in claim 4 which further includes forming the spaced through apertures in the lip of greater diameter than the bore in the tubular member end, and with the tubular members positioned on the underside of the lip members formed with tubular extensions sized to be a snug fit in said greater apertures formed in the lip.

7. A compact disposable delivery system comprising
a disposable fluid infusion device including a housing for a supply of fluid having an inlet aperture for the fluid, a piston slidably mounted in said housing, and an elastomeric tubing for biasing said piston towards said outlet aperture from a stretched condition thereof to exhaust fluid therethrough under pressure;
a restrictor for controlling fluid flow from said outlet aperture of said housing;
a disposable pressure transducer connected to said outlet aperture of said housing of said infusion device to receive pressurized fluid therefrom;
a catheter connector connected to said transducer to receive pressurized fluid therefrom and to deliver blood pressure pluses thereto; and
a recording device electronically connected with said transducer to receive signals therefrom corresponding to the received blood pressure pulses.

8. A system as set forth in claim 7 which further comprises a flexible conduit between said transducer and said outlet aperture of said housing and a clamp means in said conduit.

9. A system as set forth in claim 7 wherein said means transducer has plug means for selectively receiving wire means extending from said recording device.

10. A system as set forth in claim 7 wherein said transducer is disposed six inches or less from said catheter connector.

* * * * *

UNITED STATES PATENT AND TRADEMARK OFFICE
CERTIFICATE OF CORRECTION

PATENT NO. : 4,936,832

DATED : June 26, 1990

INVENTOR(S) : VINCENT L. VAILLANCOURT

It is certified that error appears in the above-identified patent and that said Letters Patent is hereby corrected as shown below:

Column 8, line 22 change "the grasping" to -and grasping-
Column 8, line 35 change "73 are depicted" to -73 as depicted-
Column 9, line 1 change "cluff" to -cuff-
Column 9, lines 10 and 11 change "coductors" to -conductors-
Column 9, line 37 change "to noted" to -to be noted-
Column 10, line 46 change "to be broadest" to -to the broadest- Signed and Sealed this Twenty-ninth Day of October, 1991

Attest:

HARRY F. MANBECK, JR.

Attesting Officer

Commissioner of Patents and Trademarks